United States Patent [19]

Blair et al.

[11] 4,078,972

[45] Mar. 14, 1978

[54] METHOD OF PURIFICATION OF CARBOXYPEPTIDASE $G_1$

[75] Inventors: Henry E. Blair, Barnstable; Enrique Junowicz, Brookline, both of Mass.

[73] Assignee: Trustees of Tufts College, Inc., Boston, Mass.

[21] Appl. No.: 697,422

[22] Filed: Jun. 18, 1976

[51] Int. Cl.² .......................................... C07G 7/028
[52] U.S. Cl. ................................................ 195/66 R
[58] Field of Search .............................. 195/62, 66 R

[56] References Cited

PUBLICATIONS

McCullough et al., Journal of Biological Chemistry, vol. 246, No. 10, pp. 7207-7213 (1971).

Uren, Biochimica et Biophysica Acta, vol. 236, (1971), pp. 67-73.

*Primary Examiner*—Lionel M. Shapiro
*Attorney, Agent, or Firm*—Richard P. Crowley

[57] ABSTRACT

A method of purifying a protein-reaction mixture to obtain carboxypeptidase $G_1$, which method comprises: passing the mixture through a column containing support material, such as carboxymethyl cellulose, under pH conditions such that the carboxypeptidase $G_1$ is preferentially and selectively bonded to active sites on the support material in preference to other protein materials of the mixture; displacing the bound carboxypeptidase $G_1$ by an eluant, such as a glutamate, which has a greater affinity for the carboxypeptidase $G_1$ than the support material; and recovering from the column a mixture of the eluant and the carboxypeptidase $G_1$.

10 Claims, 1 Drawing Figure

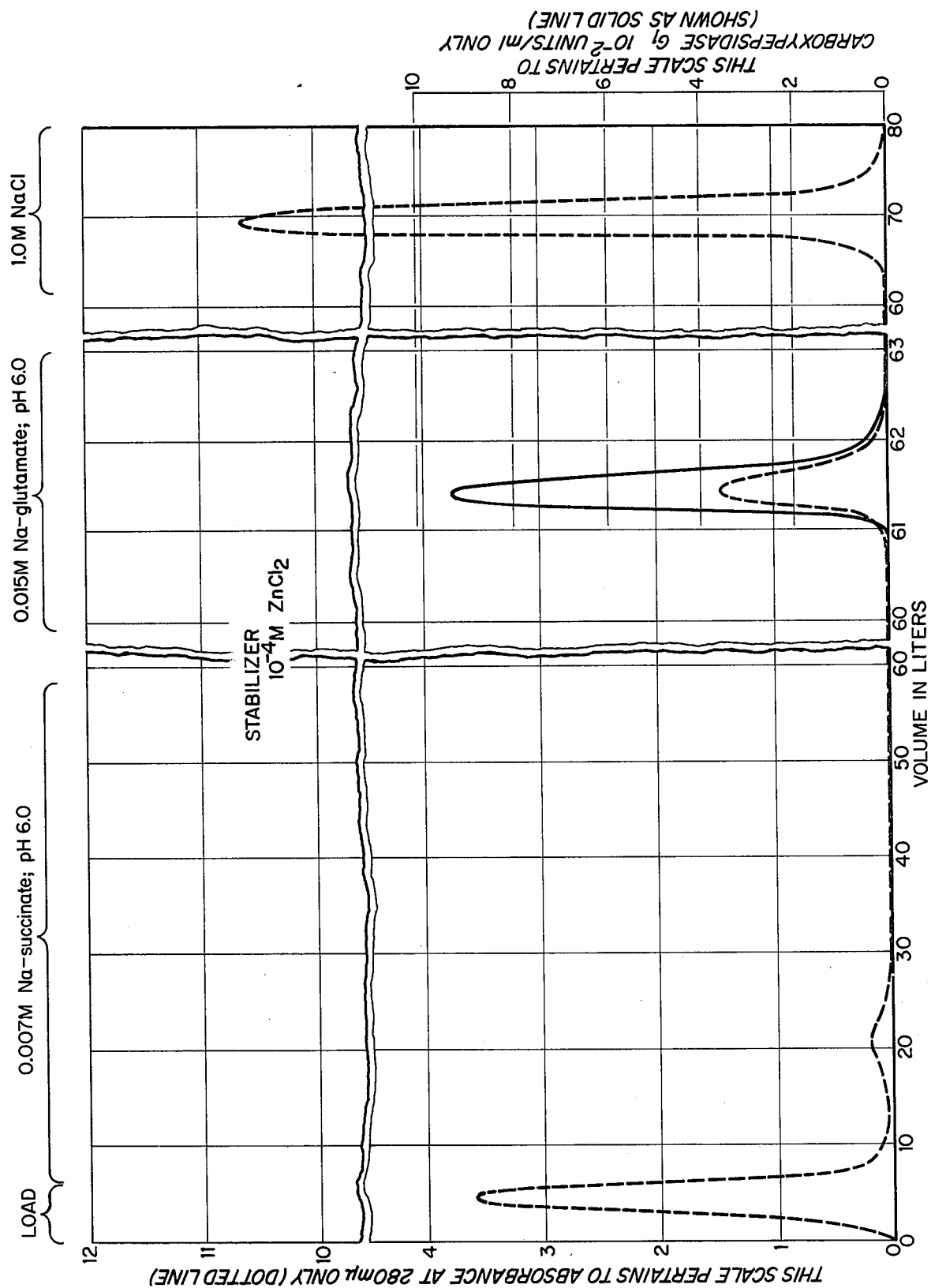

METHOD OF PURIFICATION OF CARBOXYPEPTIDASE G₁

BACKGROUND OF THE INVENTION

Folate antagonists, particularly methotrexate, have become important drugs in the treatment of certain human malignancies. Methotrexate (4-amino-$N^{10}$-methylpteroylglutamic acid) is chemically similar to folic acid and its derivatives (particularly 5-methyltetrahydrofolate in human tissue) and interferes with folic acid and derivatives thereof to interrupt folate metabolism in the synthesis of DNA in the body. A specific example is the inhibition of enzyme dihydrofolate reductase caused by methotrexate. This process inhibits folate metabolism and thereby the synthesis of DNA.

The primary use of the enzyme is for the depletion of serum folates. A secondary use is in methotrexate rescue. Where methotrexate has worked in the body for an optimum time, it is necessary to stop its work in human tissue, since death is caused by too high a concentration of methotrexate in the human body for too long a period of time.

An enzyme, carboxypeptidase $G_1$ (hereinafter designated as "$G_1$"), has been isolated which hydrolyzes the carboxyl-terminated glutamate from both reduced and nonreduced folate derivatives. The enzyme, $G_1$, specifically breaks down the methotrexate and serum folates which then become inactive.

Attempts to purify the reaction mix and to obtain the particular carboxypeptidase $G_1$ by conventional techniques have proved inadequate, probably due to the similar chemical structure and molecular weight of other protein materials in the crude reaction mixture. There is a need then to provide a simple, rapid and inexpensive method of separating carboxypeptidase $G_1$ from the preparative reaction mix.

A method of preparing $G_1$ containing a reaction mixture is described in the article "Purification and Properties of Carboxypeptidase $G_1$," by J. L. McCullough et al, The Journal of Biological Science, Vol. 246, No. 23, pages 7207–7213, herein incorporated by reference.

SUMMARY OF THE INVENTION

Our invention relates to a method for the purification and/or concentration of a protein from a mixture of proteins, such as a crude reaction mixture. In particular, our invention concerns the purification of enzymes like carboxypeptidase, such as $G_1$, from a crude reaction mixture containing the enzyme and to the product produced by the method.

We have discussed that a selected protein from a mixture of proteins, and optionally other products as might be present in a crude reaction mixture produced by a microorganism, may be concentrated and purified in a rapid, simple and inexpensive technique. Our method comprises: preferentially and selectively binding the selected enzyme protein to a support material containing sites which complex with or bind the protein molecule; displacing the bound protein with an eluant which is selected to have a higher affinity for the bound protein than the support material; and recovering the eluant and selected protein mixture. The protein is then recovered by conventional recovering methods from the eluant protein mixture.

In one embodiment, the enzyme, carboxypeptidase $G_1$, is purified from a crude reaction mixture containing the $G_1$, such as a reaction mixture obtained by the method in the McCullough et al publication, supra. The crude reaction mixture contains a mixture of proteins from which it is most difficult to separate the $G_1$ by other methods. Our method for purifying the $G_1$ enzyme includes passing the crude reaction mixture through a column containing gel or particulate support material with active carboxyl groups under selected pH conditions, such that the $G_1$ is selectively complexed or bound to the active sites of the support material in preference to the other components in the mixture. Our method then includes displacing the bound $G_1$ by passing an eluant, such as a carboxyamino acid or acid salt, through the column, the carboxyamino material having a greater affinity and binding or complexing degree than the $G_1$ to the support material. Our method then includes recovering the carboxyamino-$G_1$ mixture and recovering the $G_1$ from such mixture.

The protein mixture from which the selected protein is to be recovered or purified may be derived from a variety of natural and synthetic sources, such as pharmaceutical waste and by-products, pure protein mixtures, crude reaction mixtures of protein derived from microorganism reaction and cultures and the like.

The support material may be placed in contact with the protein mixture by any method of contact; however, typically and preferentially, the support material is placed in a column as a packing, and contact is achieved by passing the protein mixture through the column, for example, by gravity or under pressure. The support material is usually in finely divided particle or gel form which permits the passage of the liquid protein mixture in solution or suspended form.

The nature of the support material may vary, provided only that it contains active sites or otherwise complexes and binds only or preferentially the selected protein under the pH conditions of the method. Typically, the support material would comprise a compound which has a plurality of acidic groups or sites, such as carboxy groups. One class of materials found to be useful as support materials is carboxylated cellulosic materials, such as carboxymethyl cellulose. Other materials would include, but not be limited to, carboxyethyl and carboxypropyl; e.g., alkyl, cellulose and mixtures and combinations thereof, as well as various synthetic polymers, such as used in ion-exchange columns like acrylate resins with free acid groups, of which bind the amino carboxy groups of the selected protein.

In the preferred and optimum embodiment, the pH of the mixture in the column is adjusted and maintained at a selected pH or pH range, so that the protein is weakly bound to the support material. The optimum pH is easily determined, and, for example, with $G_1$ is about 6.0, with carboxymethyl cellulose as a support material. At a pH of less than about 6.0, the $G_1$ is unstable, while at a pH of above 6.0, the protein $G_1$ is not fully charged and, therefore, exhibits less affinity for the support material. If desired, other factors, such as the amino-acid concentration, may be adjusted to regulate the optimum binding pH of the protein. In the purification of $G_1$, the method is carried out with a solution which contains a zinc ion; e.g., $1 \times 10^{-4}$ molar, since $G_1$ is unstable in the absence of zinc ion.

The eluant solution used to displace the bound protein is selected to be a compound, typically an acidic compound, preferably an amino acid, which has a greater degree of affinity for the protein than the support material, so that the protein is displaced and from which the displaced protein may be easily or rapidly removed. The eluant is usually a pH-buffered solution and, for example, also contains a zinc-ion concentration in the purification of $G_1$. The eluant material preferentially is an amino acid or an amino salt, such as glutamic acid, or the soluble salts, such as sodium or potassium glutamate, and similar low-molecular weight amino acids. Such amino acids would comprise amino alkane polycarboxylic acids and salts; for example, amino $C_3$-$C_6$ alkane di or tri carboxylic acids and their salts. Often, a review of the literature or the publication covering the support material will provide degrees of affinity for various amino acids for the support material and for the protein, so that a selection of the desired eluant can be made or the choices narrowed to a few materials to be tested. Glutamic acid or sodium glutamate is a desired eluant for $G_1$, although other carboxyamino acids and acid salts may be employed. The eluant solution is passed through the column by gravity or under pressure, with the column worked one, two, three or more times until all the bound protein is removed, and the eluant-protein solution mixture recovered.

The protein is then separated from the eluant, such as, for example, by gel filtration, reverse osmosis, dialysis, fractionation, electrophoresis, or other separation and purification methods, to permit the recovery of the protein and the reuse, if desired, of the eluant in the method.

In operation, a chromatographic column is packed with the support material and the support material is equilibrated with a buffer solution to the desired pH, and with a metal ion or other material, if required, as a stabilizer for the protein. The protein mixture is then poured into the column and the column worked several times with a buffer solution until all the unbound protein of the protein mixture is washed from the column. The buffered, stabilized eluant solution is then passed through the column several times, and the resulting mixture is recovered and the protein removed from this eluant-protein mixture.

Our method will be described for the purpose of illustration only in connection with the purification of carboxypeptidase $G_1$ from a reaction mixture; however, it is recognized and is within the spirit and scope of our invention that other proteins may be purified from other protein mixtures by the same or a similar method, and by changes and modifications to our method within the skill of the art.

BRIEF DESCRIPTION OF THE DRAWING

The DRAWING is a schematic, graphical representation showing our method of the purification of carboxypeptidase $G_1$.

DESCRIPTION OF THE EMBODIMENTS

A crude reaction mixture of protein containing carboxypeptidase $G_1$ was prepared as set forth in the McCullough et al publication, supra.

Reaction cells (9Kg) were suspended in two volumes (1 g/l) of tris - Zn buffer (0.01 M tris Cl - $10^{-5}$ M $ZnCl_2$, pH 7.3) and passed through a laboratory homogenizer four times. Three additional cell volumes (27 l) of tris - Zn buffer were added to the suspension, and the pH adjusted to 7.3 with 1 N NaOH. Gross cell debris was removed in a centrifuge (14,000 × g, 20 l/hr), and the supernatant clarified in an ultracentrifuge with an RK 6 rotor (80,000 × g, 17 l/hr).

A one percent solution of protamine sulfate (22 l) was added to the clarified extract (39 l) in a ratio of 1.0g of protamine sulfate per 3 g of protein. The resulting suspension was stirred for 45 minutes and centrifuged in a centrifuge as above. The precipitate, which contained the bulk of the nucleic acids, was discarded.

The protamine sulfate supernatant (58 l) was brought to 55% saturation with solid ammonium sulfate (321 g/l). The suspension was stirred for 30 minutes and centrifuged batchwise for 10 minutes. The precipitate was discarded and the supernatant (66 l) brought to 80% saturation with solid ammonium sulfate (22.4 lbs). The suspension was stirred for 30 minutes, and centrifuged in an ultracentrifuge with an RK 3 rotor (40,000 × g, 20 l/hr). The supernatant was discarded and the precipitate dissolved in approximately its volume of tris - zinc buffer. The solution was desalted on a 7 l G-25 column (10 × 100) (two runs 700 ml/run). The precipitate which formed during desalting was removed by centrifugation (10,000 × g, 30 min.).

The clarified sample (3.8 l) was mixed with a swollen cake of QAE Sephadex A50 (50 g dry weight) which was equilibrated with tri - Zn buffer. The suspension was stirred for 30 minutes and filtered on a buchner funnel. The filter cake, which was not allowed to dry, was subsequently washed with tris - Zn buffer (4000 ml). The initial unabsorbed solution and the buffer wash were pooled, and the filter cake discarded.

The unabsorbed protein solution (7.9 liter) was brought to 85% saturation with solid ammonium sulfate (559 g/l). The suspension was stirred for 30 minutes and centrifuged in an ultracentrifuge (40,000 × g, 20 l/hr). the supernatant was discarded and the precipitate was dissolved in a minimal volume of a succinate - Zn buffer (0.005 M Na succinate - $10^{-4}$ M $ZnCl_2$, pH 6.0). The solution (775 ml) was desalted on the G-25 column as above (387 ml sample per run). The precipitate which formed during desalting was removed by centrifugation (10,000 × g, 30 minutes). The supernatant (approximately 3000 ml) was stored frozen.

The desalted frozen supernatant sample was thawed and applied to a (14 × 50) CM column packed by single decantation with microgranular carboxymethyl cellulose equilibrated with 0.005 M Na succinate - $10^{-4}$ M $ZnCl_2$ (pH 6.0) buffer solution. The support material was CMC 52 from Whatman Limited. The column was washed with one column volume of starting buffer solution, and then extensively washed (7 - 10 column volumes) with 0.007 M Na succinate - $10^{-4}$ M $ZnCl_2$ (pH 6.0) to remove all unbound protein from the column, with the carboxypeptidase $G_1$ then bound to the carboxyl-active sites of the CMC support material. Determination of the removal of unbound protein may be made by measuring the optical density (OD) at 280 m$\mu$ of the column wash effluent with a spectrophotometer. Washing is carried out until the OD at 280 m$\mu$ is less than 0.010 OD.

The bound carboxypeptidase $G_1$ was then eluted with a 0.015 M sodium glutamate - $10^{-4}$ M $ZnCl_2$ (pH 6.0) solution, the amino acid glutamate having a greater affinity for the $G_1$ than the $G_1$ has for the CMC, thereby displacing the $G_1$ from the CMC column support material. The eluant flow rate throughout the operation of the column was approximately 2.5 l per hour. Fractions of 800 ml volume were collected during the loading and washing procedures, while fractions of approximately 220 ml were collected during the elution of the enzyme. The peak fractions containing homogeneous carboxypeptidase $G_1$ were pooled and stored frozen for later separation of the $G_1$ by gel filtration.

The drawing graphically depicts the purification process for carboxypeptidase $G_1$. Absorbence (in this particular case 280 m$\mu$) is plotted against the volumes of the various liquids passing through the chromatographic column during the purification. The dotted line represents the change in absorbence as the impure protein mixture is first loaded on the carboxymethyl cellulose in the column and then eluted with sodium glutamate to displace the carboxypeptidase $G_1$ fraction, and finally washed with a sodium-chloride solution to remove other proteins from the carboxymethyl cellulose. The solid line quantitatively represents the amount of purified carboxypeptidase $G_1$.

Table I contains data from specific purifications of carboxypeptidase $G_1$ using carboxymethyl cellulose. Activity is represented in units and unit percentage, and is determined by the methods explained in the publication, supra.

TABLE I

Affinity Elution of Carboxypeptidase $G_1$ on Carboxymethyl Cellulose

|  | RUN A | RUN B* |
|---|---|---|
| Column dimensions, cm | 14 × 50 | 7 × 20 |
| Column volume, liters | 7.7 | 0.8 |
| Flow rate, liters/hour | 2.5 | 0.5 |
| Fractions collected (milliliters), load and wash | 1600 | 200 |
| Fractions collected (milliliters), enzyme elute | 220 | 22 |
| Activity loaded, units[1]) | 5.7 × 10$^5$ | 1.2 × 10$^5$ |
| Activity recovered, percent | 95 | 102 |
| Activity recovered by affinity elution, percent | 61 | 95 |
| Specific activity loaded, units per milligram of protein | 16.0 | 16.0 |
| Specific activity recovered by affinity, units per milligram of protein elutes | 670.0 | 770.0 |
| Purification, fold | 42 | 48 |

*Average of two identical runs
[1])units = micromoles of substrate hydrolyzed per minute

What we claim is:

1. A method of obtaining a purified carboxypeptidase $G_1$ from a protein mixture containing the carboxypeptidase $G_1$, which method comprises:
    (a). contacting the protein-containing mixture with a carboxyalkyl cellulosic support material under pH conditions, such that the carboxypeptidase $G_1$ is complexed selectively and bound preferentially to the cellulosic material in preference to other proteins in the protein mixture;
    (b). displacing the bound carboxypeptidase $G_1$ from the cellulosic material by contacting the bound carboxypeptidase $G_1$ with an amino acid eluant which has a greater affinity for the carboxypeptidase $G_1$ than the carboxypeptidase $G_1$ has for the cellulosic material; and
    (c). recovering an admixture of the carboxypeptidase $G_1$ and eluant.

2. The method of claim 1 wherein the contacting and displacing steps are carried out in a pH-buffered solution of about 6.0 and in the presence of a stabilizing amount of a zinc ion.

3. A method of obtaining a purified carboxypeptidase $G_1$ from a crude protein-containing reaction mixture derived from Pseudomonas stutzeri containing the carboxypeptidase, which method comprises:
    (a) passing the crude mixture containing the carboxypeptidase $G_1$ into contact with a carboxymethylcellulose support material to bind preferentially the $G_1$ to the support material in preference to the other proteins in the crude mixture;
    (b) displacing the bound carboxypeptidase $G_1$ from the support material by passing a glutamic acid or acid salt eluant into contact with the bound carboxypeptidase $G_1$ and in the presence of a stabilizing amount of zinc ion;
    (c) maintaining the pH, during the passing and displacing steps, at a pH of about 6.0; and
    (d) recovering a glutamic acid or acid salt and carboxypeptidase-$G_1$ mixture.

4. The method of claim 1 wherein the protein mixture comprises a crude reaction mixture of proteins extracted from a strain of Pseudomonas stutzeri.

5. The method of claim 1 wherein the support material is a carboxymethyl cellulose.

6. The method of claim 1 wherein the eluant comprises a pH-buffered solution of glutamic acid or an acid salt thereof.

7. The method of claim 1 wherein the pH, during the contacting and displacing steps, is maintained at about 6.0.

8. The method of claim 1 which includes the step of recovering the carboxypeptidase $G_1$ from the mixture.

9. The method of claim 8 wherein the carboxypeptidase $G_1$ is recovered by a gel-filtration method.

10. The method of claim 3 which includes recovering the carboxypeptidase $G_1$ from the glutamic acid mixture.

* * * * *